(12) United States Patent
Breuer et al.

(10) Patent No.: US 7,675,028 B2
(45) Date of Patent: Mar. 9, 2010

(54) LOW-SCATTERING FOAM PHANTOM FOR MOLECULAR IMAGING

(75) Inventors: Johannes Breuer, Dortmund (DE); Rainer Paul, Kapsweyer (DE); Volker Matschl, Knoxville, TN (US); A. Andrew Carey, Rockford, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/144,063

(22) Filed: Jun. 23, 2008

(65) Prior Publication Data

US 2009/0314933 A1    Dec. 24, 2009

(51) Int. Cl.
*G01D 18/00* (2006.01)
(52) U.S. Cl. .................................. 250/252.1
(58) Field of Classification Search .............. 250/252.1, 250/370.01–370.15; 378/18, 98.8; 434/272
See application file for complete search history.

(56) References Cited

U.S. PATENT DOCUMENTS

| | | | |
|---|---|---|---|
| 5,227,627 A * | 7/1993 | Gamarnik et al. | 250/252.1 |
| 6,490,336 B1 * | 12/2002 | Suess et al. | 378/18 |
| 6,744,039 B1 * | 6/2004 | DiFilippo | 250/252.1 |
| 7,449,681 B1 * | 11/2008 | Rappoport et al. | 250/252.1 |
| 2003/0220718 A1 * | 11/2003 | Jaszczak et al. | 700/282 |
| 2008/0298540 A1 * | 12/2008 | Serban et al. | 378/18 |

OTHER PUBLICATIONS

Hold et al., "Multimodal PET/Ultrasound Imaging for Cardiac Molecular Imaging," 2007, IEEE Ultrasound Symposium, pp. 1472-1475.*
Wassenaar et al., "Characterization of PET Partial Volumne Corrections for Variable Myocardial Wall Thicknesses," @006, IEEE Transactions on nuclear science, vol. 53, No. 1, pp. 175180.*
Huber et al., "Multi-Modality Phantom Development," 2007, IEEE Nuclear Science Symposium Conference Record, pp. 2944-2948.*
Hamill et al., "A 68Ge PET hot-sphere phantom with no cold shells," 2005, IEEE Nuclear Science Symposium Conference Record, pp. 1606-1610.*
Oakes et al., "Normalization in 3D PET: Comparison of detector efficiencies obtained from uniform planar and cylindrical sources," Nov. 9-15, 1997, IEEE Nuclear Science Symposium, vol. 2, pp. 1625-1629.*

* cited by examiner

*Primary Examiner*—David P Porta
*Assistant Examiner*—Kiho Kim
(74) *Attorney, Agent, or Firm*—Peter L. Kendall

(57) ABSTRACT

A phantom for use in generating a normalization data set to be used in PET scanning (particularly integrated MR/PET scanning) is disclosed. The phantom features radiation activity distributed throughout a foam material. The foam—e.g., a polyurethane foam—may be produced by reacting two liquids, one of which is emulsified with water in which $Ge^{68}$ has been dissolved. The foam produced thereby exhibits uniform distribution of radioactivity and a long mean free path for 511 keV gamma particles—two attributes that are important attributes of a PET phantom.

29 Claims, 3 Drawing Sheets

LOW-SCATTERING FOAM PHANTOM FOR MOLECULAR IMAGING

TECHNICAL FIELD

In general, the invention relates to nuclear medicine. More particularly, the invention relates to phantoms used for normalization or calibration measurements of nuclear medical imaging devices as well as for daily quality control measurements of such devices.

BACKGROUND

Positron emission tomography (PET) does not measure three-dimensional images of an observed object or subject directly. Instead, a small dose of a positron emitter within the object or subject is brought into the field of view (FOV) of the scanner. Positrons that are generated during a scan can only travel a few millimeters until they annihilate with an electron of the surrounding matter. In this process, a pair of simultaneous gamma particles each with an energy of 511 keV is generated, which gamma particles travel nearly perfectly in opposite directions. The gamma particles can be stopped and detected by means of a large number of small scintillator crystals. The PET scanner accumulates the detected coincident light events between all possible crystal pairs into "line of response" or LOR bins. The three-dimensional distribution of the positron emitter within the FOV can then be reconstructed from the accumulated LORs by a suitable reconstruction algorithm.

Prior to such reconstruction, a series of pre-processing steps has to be performed, including a "normalization" step which corrects for variations in the counting efficiencies of different crystal pairs. This normalization procedure removes artifacts from the reconstructed images and results in a much smoother appearance of the images. To determine the correction factors, it is necessary to measure a phantom that uniformly fills the PET scanner field of view with radioactivity. The normalization or correction factors are then the ratio between expected and actually measured count rates.

Additionally, a phantom may be used for daily quality control measurements of the scanning machinery. By imaging the phantom with its known geometry and radiation distribution, the accuracy of the software used to assemble the various tomographic slices acquired by the imaging apparatus into three-dimensional representations of a patient's region of interest can be assessed and, if necessary, the various apparatus settings can be adjusted.

Optimally or ideally, a normalization phantom should exhibit the same amount of radioactivity along every possible pathway (i.e., LOR) between two crystals. In practice or realistically, however, a phantom may be used so long as it satisfies the following three criteria:

a) the coefficients of scattering or absorption of 511 keV gamma rays generated within the phantom should be as small as possible;

b) every monitored LOR of the scanner must intersect with the radioactive region of the phantom (which includes typically all LORs that intersect with the field of view of the PET scanner); and c) the geometry and positioning of the phantom have to be known exactly, such that software can correct for the non-uniformity of the amount of radio-activity between the detector crystal pairs.

Usually, phantoms with uniform distribution of a radioactive substance are filled with solid plastic materials that can be produced by a curing process of one or more liquids into which a radioactive substance is injected while the material is still liquid. If the materials are mixed properly, the radioactivity is perfectly uniformly distributed throughout the phantom. Unfortunately, however, the attenuation length of the commonly used plastic materials is very short. For example, typical polyethylene-based plastics with a density of around 1.1 g/cc have an attenuation length of about 9 to 10 cm and a Compton scattering fraction of nearly 100 percent. Therefore, it is not possible to build larger phantoms, which could flood the entire field of view, that do not suffer from unacceptably high absorption/scattering.

To compensate for that limitation, it is known to sweep one or more smaller phantoms through the field of view during the normalization scan. For example, two cylindrical phantom rods may be fixed parallel to each other and rotated or orbited by means of an electric motor about the parallel line (axis) that extends between the two of them. Averaged over time, the sweep generates a cylindrical "net" or overall phantom that fills the field of view yet that exhibits no or minimal scattering or absorption of 511 keV gamma rays.

Recently, however, an integrated magnetic resonance/PET (or MR/PET) scanner has been developed (see, e.g., U.S. Pub. No. 2007/0055127, published Mar. 8, 2007 and incorporated herein by reference), and ordinary electric motors do not operate properly within the strong magnetic field produced by the MR components of the apparatus. Accordingly, the current state of the art teaches that the PET components of the integrated apparatus must be separated from the MR components of the apparatus when the phantom-based normalization data set is being acquired. Such protocol, however, is inconvenient as well as time- and space-consuming. Moreover, it carries with it the risk that the various apparatus setup parameters may be changed during the disassembly and reassembly process.

SUMMARY

The invention provides a phantom that may be used to circumvent such drawbacks of the current state of the art. More particularly, in one aspect, the invention features a phantom that is filled with radioactive foam. One suitable base material is polyurethane foam formed by reacting two liquids, one of which is emulsified with water in which $Ge^{68}$ has been dissolved. The foam produced thereby exhibits uniform distribution of radioactivity and a long mean free path for 511 keV gamma particles—two attributes that are important attributes of a PET phantom. Suitably, the phantom is configured as either a completely filled or a hollow cylinder.

In another aspect, the disclosure discloses a method for obtaining a normalization data set used to compensate for non-uniformities of a PET scanner. The method entails placing uniformly radioactive foam in the field of view of the scanner; scanning the foam to obtain a PET scan data set; and analyzing the PET scan data set to derive normalization coefficients therefrom.

In another aspect, the disclosure discloses a method for quality control testing a PET scanner. The method entails placing uniformly radioactive foam in the field of view of the scanner; scanning the foam to obtain a PET scan data set; and analyzing the PET scan data set to determine the accuracy with which the PET scanner imaged the phantom.

BRIEF DESCRIPTION OF THE DRAWINGS:

The disclosure will now be described in greater detail in the following by way of example only and with reference to the attached drawings, in which.

DETAILED DESCRIPTION OF AN EMBODIMENT OF THE INVENTION

Figure 1:
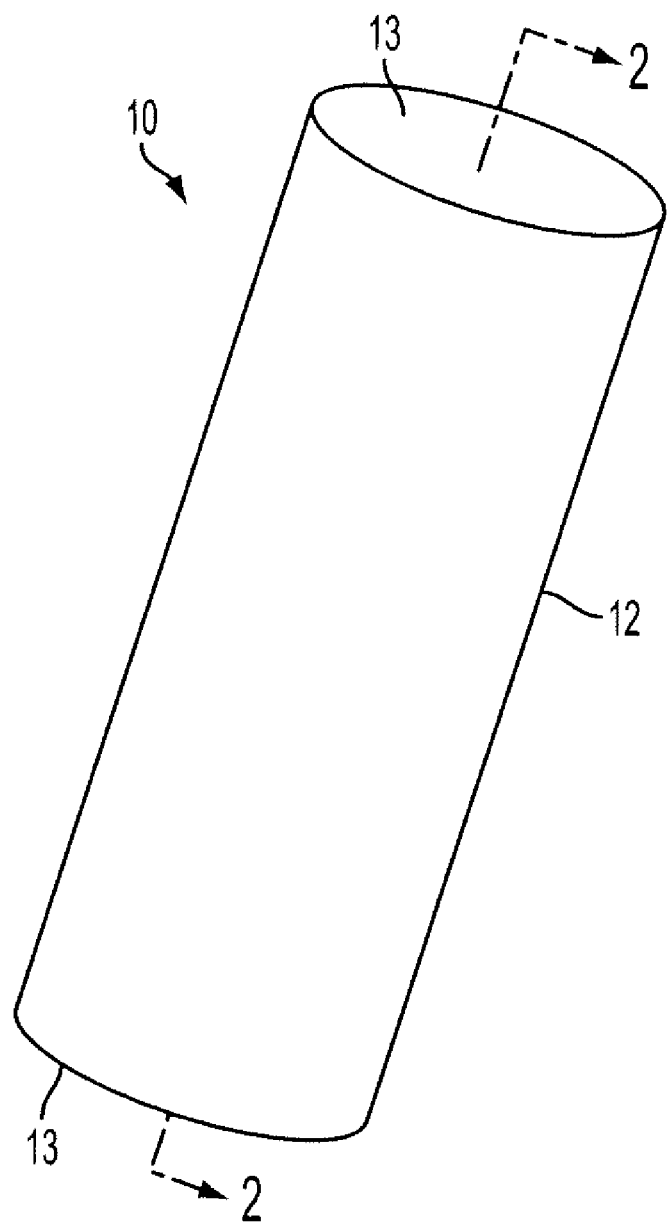
FIG. 1 is a schematic perspective view of an embodiment of a phantom according to an embodiment of the invention.
Figure 2:
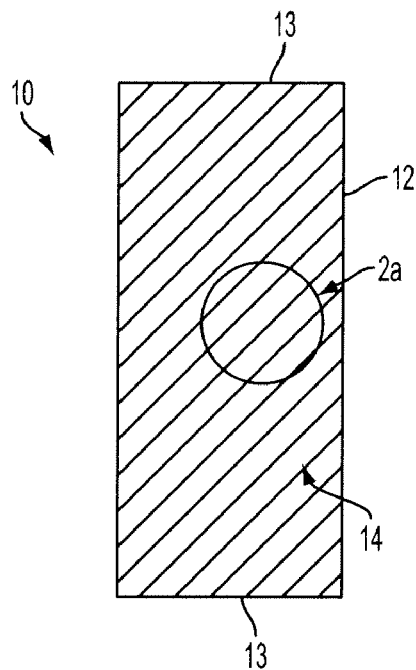
FIG. 2 is a schematic section view of the embodiment of a phantom shown in FIG. 1 taken along lines 2—2 therein.
Figure 2A:
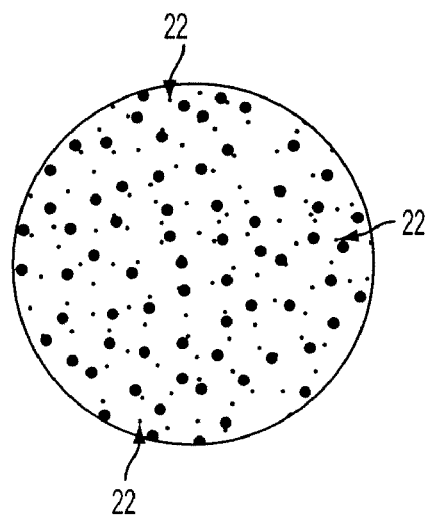
FIG. 2a is a close-up view of a portion of the phantom shown in FIG. 2.

One embodiment 10 of a phantom according to an embodiment of the invention is illustrated in FIGS. 1, 2, and 2a. As illustrated, the phantom 10 is suitably constructed from a cylinder having sidewalls 12 and end caps 13 made of radiation-transmissive material such as is known in the art. The space inside of the cylinder is filled with radioactive foam 14, i.e., foam that has radiation activity (indicated schematically by dots 22, FIG. 2a) distributed uniformly throughout it. The foam 14 is suitably polyurethane foam which may be produced conveniently through the reaction of two liquid components, one of which is emulsified with water in which $Ge^{68}$ has been dissolved.

Advantageously, the foam produced by this reaction exhibits uniform distribution of radioactivity and a relatively long mean free path for 511 keV gamma particles. Furthermore, the molecular structure is dominated by carbon and hydrogen atoms that occur in a ratio of approximately 1:2, and the total attenuation cross-section for $CH_2$ is 0.0984 $cm^2/g$. The foam has a density of approximately 0.035 $g/cm^3$. Accordingly, the attenuation length is about 290 cm (in excess of 150 cm being suitable). Given a suitable phantom diameter of 30 cm, the phantom will have a total interaction probability of 10% for gamma particles that are emitted transaxially from the center of the field of view of the PET scanner.

In terms of manufacturing the phantom, at least three approaches are envisioned. According to one approach, a bulk or block mass of radioactive foam may be produced according to the above-referenced reaction then cut to the desired shape. The foam is then inserted into the cylindrical sidewalls 12 and the end caps 13 are sealed onto the sidewalls 12.

Alternatively, a bulk or block mass of radioactive foam may be produced, which bulk material can then be ground down into smaller flakes or particles. Such flakes or particles are then introduced into the cylindrical sidewalls 12 and the end caps 13 are sealed onto the sidewalls 12. Advantageously, with this approach, one obtains a material with better homogeneity with respect to density and radioactive distribution. Moreover, a container of any arbitrary shape can be filled with such particleized material.

Still further, one may mix the constituent foam-producing liquids directly in the container. The foam would then be trimmed to remove "bleed-over" material and the container would be sealed.

The hollow cylindrical geometry of the phantom aids in reducing the fraction of absorbed and scattered gamma particles. Since the geometry of the phantom is known exactly and every line of response of the scanner intersects with the radioactive region, it is possible to scan the phantom then post-process the measured count rates to obtain a real normalization data set.

In accordance with another aspect of the invention, a PET scanner is calibrated by placing a uniformly radioactive foam in the field of view of the scanner; scanning the foam to obtain a PET scan data set; and analyzing the PET scan data set to derive normalization coefficients therefrom.

Figure 3:
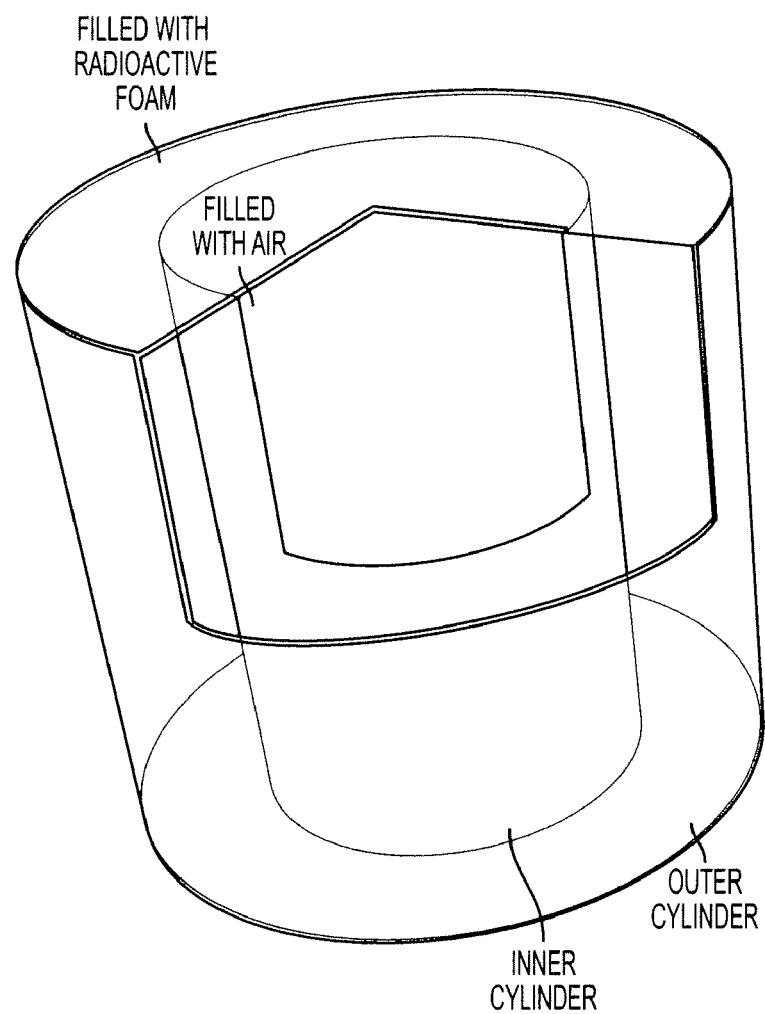
FIG. 3 is a schematic perspective view, partially in section, of an alternative embodiment of a phantom according to an embodiment of the invention.

Modifications to and departures from the disclosed embodiment will occur to those having skill in the art. For example, in an alternative embodiment illustrated in FIG. 3, a phantom according to the invention may be constructed from a comparatively thin-walled cylinder disposed within a comparatively thick-walled cylinder, with the space between the cylinders filled with radioactive foam and the inner cylinder filled with air. The embodiment illustrated in FIG. 3 has circular end caps, which seal the air space inside the inner cylinder. The thick wall of the outer cylinder can be traversed by radiation, but not by the radioactive material itself. The wall of the inner cylinder, on the other hand, can be thinner since it only holds the foam in place. If small amounts of radioactive material traverse the inner wall, no detriment should occur. With this embodiment of a phantom, a general line of response crosses the thicker wall twice and the thinner wall twice; the thinner wall may cause less absorption and scattering than the thicker wall.

These and other variations will occur to those having skill in the art. Accordingly, what is protected is defined by the scope of the following claims.

What is claimed is:

1. A phantom for use in connection with calibration of a nuclear medicine imaging device, comprising:
    a radioactive foam material with radiation activity distributed uniformly throughout the foam material, wherein said phantom is used for calculation of a normalization data set.

2. The phantom of claim 1, wherein the radiation activity is provided by $Ge^{68}$.

3. The phantom of claim 1, wherein the foam is polyurethane foam.

4. The phantom of claim 1, wherein the phantom exhibits a gamma attenuation length in excess of 150 cm.

5. The phantom of claim 4, wherein the phantom exhibits a gamma attenuation length of about 290 cm.

6. The phantom of claim 1, wherein the phantom comprises an inner cylinder disposed coaxially within an outer cylinder and the foam is disposed between the inner and outer cylinders.

7. The phantom of claim 6, wherein the inner cylinder has thinner walls than the outer cylinder.

8. The phantom of claim 7, further comprising circular end caps sealing the space between the inner and outer cylinders as well as the space within the inner cylinder.

9. The phantom of claim 1, wherein the nuclear medicine imaging device comprises a PET scanner.

10. The phantom of claim 1, wherein the foam material is housed within a container.

11. The phantom of claim 10, wherein the foam material is particleized.

12. The phantom of claim 10, wherein the foam material has been cut to conform to the contours of the container.

13. The phantom of claim 10, wherein the foam material has been produced directly in the container.

14. A method for calibrating a PET scanner, comprising:
    placing a radioactive foam phantom in the field of view of the scanner, wherein radiation activity is distributed uniformly throughout the foam material;
    scanning the foam to obtain a PET scan data set; and
    analyzing the PET scan data set to derive normalization coefficients therefrom.

15. The method of claim 14, wherein radiation activity of the foam is provided by $Ge^{68}$.

16. The method of claim 14, wherein the foam is polyurethane foam.

17. The method of claim 14, wherein the phantom exhibits a gamma attenuation length in excess of 150 cm.

18. The method of claim 14, wherein the phantom exhibits a gamma attenuation length of about 290 cm.

19. The method of claim 14, wherein the phantom comprises an inner cylinder disposed coaxially within an outer cylinder and the foam is disposed between the inner and outer cylinders.

20. The method of claim 19, wherein the inner cylinder has thinner walls than the outer cylinder.

21. The method of claim 20, wherein the phantom further comprises circular end caps sealing the space between the inner and outer cylinders as well as the space within the inner cylinder.

22. A method for quality control testing a PET scanner, comprising:
   placing a radioactive foam phantom in the field of view of the scanner, wherein radiation activity is distributed uniformly throughout the foam material;
   scanning the radioactive foam to obtain a PET scan data set; and
   analyzing the PET scan data set to derive normalization coefficients therefrom and determine the accuracy with which the PET scanner imaged the phantom.

23. The method of claim 22, wherein radiation activity of the foam is provided by $Ge^{68}$.

24. The method of claim 22, wherein the foam is polyurethane foam.

25. The method of claim 22, wherein the phantom exhibits a gamma attenuation length in excess of 150 cm.

26. The method of claim 22, wherein the phantom exhibits a gamma attenuation length of about 290 cm.

27. The method of claim 22, wherein the phantom comprises an inner cylinder disposed coaxially within an outer cylinder and the foam is disposed between the inner and outer cylinders.

28. The method of claim 27, wherein the inner cylinder has thinner walls than the outer cylinder.

29. The method of claim 28, wherein the phantom further comprises circular end caps sealing the space between the inner and outer cylinders as well as the space within the inner cylinder.

\* \* \* \* \*